US008618067B2

(12) United States Patent
Caswell et al.

(10) Patent No.: US 8,618,067 B2
(45) Date of Patent: *Dec. 31, 2013

(54) L-SUGAR COLON CLEANSING AGENT AND USES THEREOF

(75) Inventors: Michael Caswell, Lynchburg, NJ (US);
Edward Delaney, Princeton, NJ (US);
Mohammad Rahman, Lynchburg, VA (US)

(73) Assignee: Aptalis Pharma US, Inc., Bridgewater, NJ (US)

( * ) Notice: Subject to any disclaimer, the term of this patent is extended or adjusted under 35 U.S.C. 154(b) by 474 days.

This patent is subject to a terminal disclaimer.

(21) Appl. No.: 12/793,512

(22) Filed: Jun. 3, 2010

(65) Prior Publication Data

US 2011/0053867 A1  Mar. 3, 2011

Related U.S. Application Data

(60) Provisional application No. 61/183,596, filed on Jun. 3, 2009, provisional application No. 61/233,722, filed on Aug. 13, 2009.

(51) Int. Cl.
*A61K 31/70* (2006.01)
*A61K 47/00* (2006.01)
*C07H 1/00* (2006.01)

(52) U.S. Cl.
USPC ................ 514/23; 514/12; 514/892; 536/124

(58) Field of Classification Search
USPC ..................................... 536/124; 514/23, 892
See application file for complete search history.

(56) References Cited

U.S. PATENT DOCUMENTS

| 4,262,032 | A | 4/1981 | Levin |
|---|---|---|---|
| 4,581,447 | A | 4/1986 | Arena |
| 4,718,405 | A | 1/1988 | Firth et al. |
| 4,815,445 | A | 3/1989 | Swedo et al. |
| RE33,719 | E | 10/1991 | Levin |
| 5,166,193 | A | 11/1992 | Levin et al. |
| 5,219,573 | A | 6/1993 | Tarka, Jr. et al. |
| 5,624,908 | A | 4/1997 | Bicher |
| 6,638,360 | B2 | 10/2003 | Wiggins |
| 7,501,267 | B2 | 3/2009 | Izumori et al. |
| 2004/0192614 | A1 | 9/2004 | Vanner et al. |
| 2005/0129781 | A1 | 6/2005 | Skiendzielewski et al. |
| 2005/0271749 | A1 | 12/2005 | Borody et al. |
| 2009/0112002 | A1 | 4/2009 | Weymouth-Wilson et al. |

FOREIGN PATENT DOCUMENTS

| EP | 423771 A2 | 4/1991 |
|---|---|---|
| EP | 1108792 A1 | 6/2001 |
| WO | WO 2008/053206 | 5/2008 |
| WO | WO-2009/157810 | 12/2009 |

OTHER PUBLICATIONS

Raymer G S et al., An Open-label Trial of L-Glucose as a Colon-cleansing Agent Before Colonoscopy, *Gastrointestinal Endoscopy*, Elsevier, NL LNKD- DOI:10.1067/MGE.2003.293, vol. 58, No. 1, Jul. 1, 2003, pp. 30-35.
U.S. Appl. No. 12/793,518, filed Jun. 3, 2010.
U.S. Appl. No. 12/962,194, filed Dec. 7, 2010.
Lundt, et al., Synthetically Useful Base-Induced Rearrangements of Aldonolactones, Department of Organic Chemistry, pp. 178-189 (2008).
Isbell, et al., Synthesis of D-Glucose-1-$C^{14}$ and D-Mannose-1-$C^{14}$, Journal of Research of the National Bureau of Standards, vol. 48, No. 3, Mar. 1952, Research Paper 2301 (pp.) 163-171.
Hsu et al., *Gastrointestinal Endoscopy*, vol. 48(3):276-282, 1998.

*Primary Examiner* — Patrick Lewis
*Assistant Examiner* — Everett White
(74) *Attorney, Agent, or Firm* — Blank Rome LLP

(57) ABSTRACT

Disclosed is L-glucose monohydrate and compositions thereof. Also disclosed are methods for making L-glucose monohydrate and compositions thereof. Further disclosed are methods for colonic cleansing using L-sugars, such as L-glucose monohydrate, and compositions and kits useful for colonic cleansing.

17 Claims, 1 Drawing Sheet

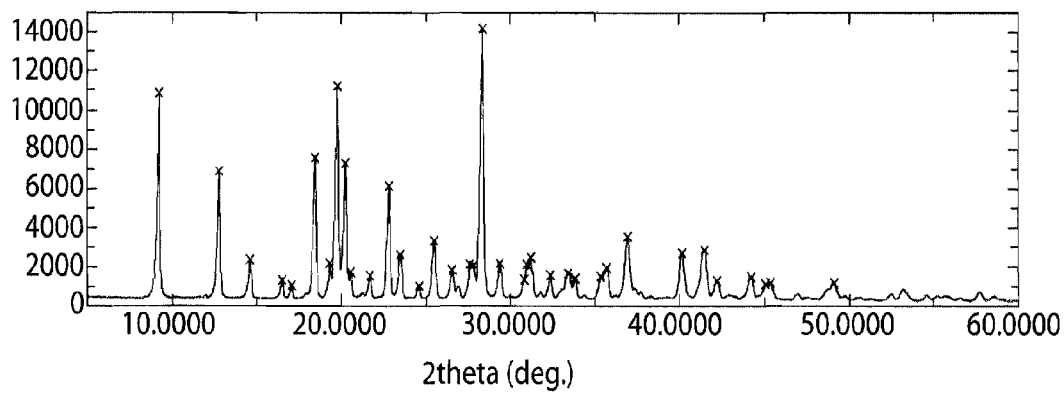
| Peak no. | 2theta | Flex Width | d-value | Intensity | I/Io | Peak no. | 2theta | Flex Width | d-value | Intensity | I/Io |
|---|---|---|---|---|---|---|---|---|---|---|---|
| 1 | 9.240 | 0.165 | 9.5631 | 10853 | 77 | 16 | 26.560 | 0.235 | 3.3533 | 1833 | 13 |
| 2 | 12.780 | 0.165 | 6.9210 | 6874 | 49 | 17 | 27.620 | 0.188 | 3.2269 | 2124 | 15 |
| 3 | 14.600 | 0.165 | 6.0621 | 2364 | 17 | 18 | 27.840 | 0.118 | 3.2019 | 2091 | 15 |
| 4 | 16.480 | 0.165 | 5.3746 | 1343 | 10 | 19 | 28.360 | 0.212 | 3.1444 | 14190 | 100 |
| 5 | 17.040 | 0.141 | 5.1992 | 1076 | 8 | 20 | 29.400 | 0.212 | 3.0355 | 2167 | 16 |
| 6 | 18.460 | 0.212 | 4.8023 | 7551 | 54 | 21 | 30.800 | 0.118 | 2.9006 | 1363 | 10 |
| 7 | 19.320 | 0.118 | 4.5904 | 2179 | 16 | 22 | 30.980 | 0.118 | 2.8842 | 2112 | 15 |
| 8 | 19.780 | 0.188 | 4.4847 | 11221 | 80 | 23 | 31.220 | 0.188 | 2.8626 | 2467 | 18 |
| 9 | 20.240 | 0.212 | 4.3838 | 7278 | 52 | 24 | 32.380 | 0.165 | 2.7626 | 1575 | 12 |
| 10 | 20.560 | 0.165 | 4.3163 | 1723 | 13 | 25 | 33.440 | 0.353 | 2.6774 | 1665 | 12 |
| 11 | 21.700 | 0.188 | 4.0920 | 1547 | 11 | 26 | 33.820 | 0.165 | 2.6482 | 1414 | 10 |
| 12 | 22.840 | 0.188 | 3.8903 | 6119 | 44 | 27 | 35.340 | 0.235 | 2.5277 | 1513 | 11 |
| 13 | 23.500 | 0.235 | 3.7825 | 2621 | 19 | 28 | 35.720 | 0.329 | 2.5116 | 1944 | 14 |
| 14 | 24.580 | 0.165 | 3.6187 | 1045 | 8 | 29 | 36.960 | 0.282 | 2.4301 | 3538 | 25 |
| 15 | 25.580 | 0.212 | 3.4875 | 3339 | 24 | 30 | 40.180 | 0.329 | 2.2425 | 2695 | 19 |
| 31 | 41.500 | 0.376 | 2.1741 | 2855 | 21 | | | | | | |
| 32 | 42.220 | 0.329 | 2.1387 | 1283 | 10 | | | | | | |
| 33 | 44.220 | 0.329 | 2.0465 | 1491 | 11 | | | | | | |
| 34 | 45.060 | 0.165 | 2.0103 | 1140 | 9 | | | | | | |
| 35 | 45.360 | 0.141 | 1.9977 | 1187 | 9 | | | | | | |
| 36 | 49.120 | 0.376 | 1.8532 | 1182 | 9 | | | | | | |

L-SUGAR COLON CLEANSING AGENT AND USES THEREOF

CROSS-REFERENCE TO RELATED APPLICATIONS

This application claims the benefit of priority to U.S. Provisional Application Nos. 61/183,596, filed Jun. 3, 2009, and 61/233,722, filed Aug. 13, 2009, both of which are incorporated herein by reference.

BACKGROUND

In 2006, an estimated 55,170 people in the United States died from colorectal cancer and 148,650 new cases were diagnosed. According to the National Cancer Institute, colon cancer is the second most deadly cancer in the United States. Of great importance in each case is early and accurate diagnosis, in which case colonoscopy is the standard tool for examination. Colonoscopy screening has been shown to reduce the expected morbidity and mortality of colorectal carcinoma by 76% to 90% (American Cancer Society. Colon and rectal cancer treatment guidelines for patients. Version 1, March 2000, (00-80M-No. 9409-HCP)). The U.S. Centers for Disease Control and Prevention estimates only an 8.5% chance of survival if the disease is diagnosed at an advanced stage.

Colon cleansing (colonoscopy preparation) is a required prerequisite for successful colonoscopy. With the requirement to identify flat lesions (nonpolypoid colorectal neoplasms) there is now an even greater need for proper colon preparation. Flat or recessed lesions are much more difficult to spot than raised polyps with traditional colonoscopy, because their appearance is similar to normal tissue. Recent research has shown that these flat lesions may be more likely to be cancerous than polyps (Soetikno et al., "Prevalence of Nonpolypoid (Flat and Depressed) Colorectal Neoplasms in Asymptomatic and Symptomatic Adults," *J. Am. Med. Assoc.* 299(9):1027-1035, 2008).

Colonoscopy preparation is commonly achieved with polyethylene glycol (PEG) solutions or oral sodium phosphate (NaP) solution or tablets. Both preparations have their limitations. Subject non-compliance because of an unpleasant taste and a necessary large fluid volume in combination with the drug ingestion has resulted in inadequate intake of PEG solution and poor colonoscopy preparation. Side effects of the PEG solution, such as bloating and nausea, are also common. Some subjects may tolerate the NaP solution or NaP tablets better than the PEG solution; however, the NaP solution has an acidic salty taste and, in addition to causing common gastrointestinal side effects, the use of NaP preparations has been associated with various fluid and electrolyte disturbances (Sharma et al., "Controlled study of pretreatment with magnesium citrate on the quality of colonoscopy preparation with polyethylene glycol electrolyte lavage solution," *Gastrointes Endosc* 46(6):541-3, 1997; Caswell et al., "The time course and effect on serum electrolytes of oral sodium phosphates solution in healthy male and female volunteers," *Can J Clin Pharmacol* 14(3):e260-74, 2007; Caswell et al., "Bowel preparation with oral sodium phosphate and renal disease," *Endoscopy.* 38(8):852, 2006; Caswell et al., "Phosphate salt bowel preparation regimens alter perioperative acid-base and electrolyte balance," *Can J Anaesth* 53(9):961, 2006).

L-glucose, the minor-image of the molecule D-glucose, cannot be metabolized by cells in the biochemical process known as glycolysis. L-glucose has been long recognized as a potential replacement for D-glucose because, like its enantiomer, it has similar organoleptic properties, i.e., sweetness and the bulk properties of D-glucose when used in food preparation.

Similarly, L-glucose has been studied for colon cleansing (colonoscopy preparation), which is a required prerequisite for successful colonoscopy. The use of L-glucose as an oral formulation for colon cleansing has been hampered by the dissolution properties of anhydrous L-glucose, the form that is currently manufactured. As such, when water is added to anhydrous L-glucose, clumping and slow dissolution are encountered. This fact has been a barrier to providing dry colon cleansing compositions to consumers for in home use. When faced with clumping and poor dissolution of L-glucose compositions, consumers may not receive the adequate dosage of L-glucose necessary to fully cleanse the colon prior to medical procedures because of the undissolved residue that remains behind in the container used to reconstitute the L-glucose containing composition.

In light of the limitations associated with currently available colonic cleansers, and the importance of proper colon preparation for colonoscopy, alternatives for colon cleansing are needed. For example, there is a need for new forms of L-glucose that are easily and more quickly dissolved in water. The compounds, compositions, methods, and kits disclosed herein address these needs and other needs.

SUMMARY

The present inventors have discovered a new rapidly dissolving form of L-glucose, specifically, L-glucose monohydrate. L-glucose monohydrate is particularly well suited as a "ready to dissolve" colon cleansing or laxative composition for home and medical use. The rapid dissolution results in easier preparation of oral solutions of L-glucose from solid L-glucose, less clumping in the solution, and more accurate dosing than anhydrous L-glucose, and, in turn, improved colon cleansing and laxative performance.

In one aspect, the present invention relates to L-glucose monohydrate and to compositions thereof (e.g., pharmaceutical compositions containing L-glucose monohydrate). Further disclosed is a method for preparing and/or isolating L-glucose monohydrate. Yet further disclosed are compositions and kits for use by consumers or medical personnel wherein a rapid, and fully dissolved solution comprising L-glucose is desired.

The present inventors have surprisingly discovered that at a sufficiently high dosage, particularly when administered as a split dose (e.g., where each dose is 36 g or greater (on the weight basis of the base L-glucose), L-sugars such as L-glucose provide enhanced colon cleansing, and can be used for colonoscopy preparation. Unlike PEG and NaP bowel cleansing preparations, L-sugars such as L-glucose have a pleasant, sweet taste, low volume intake, and an absence of or mild intensity of common cathartic-associated adverse events (AEs), making them an especially advantageous alternative to currently available preparations for colon cleansing prior to colonoscopy.

In another aspect, the present invention relates to methods of using L-sugars, such as L-glucose monohydrate, as colon cleansing agents. Further disclosed are compositions and kits containing L-sugars, such as L-glucose monohydrate, for use in colon cleansing.

One embodiment is a method for colon cleansing in a subject (such as a subject undergoing a colonoscopy) by (a) administering to the subject an aqueous solution containing from about 36 to about 72 g L-glucose (based on the weight of base L-glucose) at night (e.g., the night before the colonoscopy), and (b) administering to the subject an aqueous solution containing from about 36 to about 72 g L-glucose the following morning (e.g., the morning of, but prior to, the colonoscopy). The aqueous solutions may be prepared by dissolving a powder of L-glucose monohydrate in water.

One preferred embodiment is a method for colon cleansing in a subject (such as a subject undergoing a colonoscopy) by (a) administering to the subject an aqueous solution containing about 48 g L-glucose (based on the weight of base L-glucose) (or 52.8 g L-glucose monohydrate, which contains an equivalent amount of base L-glucose) at night (e.g., the night before a colonoscopy), and (b) administering to the subject an aqueous solution containing about 48 g L-glucose (or 52.8 g L-glucose monohydrate) the next morning (e.g., the morning of, but prior to, the colonoscopy). The aqueous solutions may be prepared by dissolving 52.8 g L-glucose monohydrate (which is equivalent to about 48 g of base L-glucose) in water (for instance 8 fluid ounces of water).

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying drawing, which is incorporated in and constitutes a part of this specification, illustrates several aspects described below.

FIG. 1 depicts the X-ray powder diffraction pattern of L-glucose monohydrate.

DETAILED DESCRIPTION

The materials, compounds, compositions, articles, devices, and methods described herein can be understood more readily by reference to the following detailed description of specific aspects of the disclosed subject matter and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

"Subject," as used herein, means an individual. In one aspect, the subject is a mammal such as a primate, and, in another aspect, the subject is a human. The term "subject" also includes domesticated animals (e.g., cats, dogs, etc.), and livestock (e.g., cattle, horses, pigs, sheep, goats, etc.).

By "rate of dissolution" and "dissolution rate" or other forms thereof is meant, the speed or quickness that a given amount of a solid fully dissolves in a given amount of water at a particular temperature.

Reference will now be made in detail to specific aspects of the disclosed materials, compounds, compositions, articles, and methods, examples of which are illustrated in the accompanying Examples.

L-Sugars

Disclosed herein are uses of L-sugars. An L-sugar is defined as a monosaccharide in which the hydroxyl group at the lowest chiral carbon atom in a Fischer projection structure is on the left.

Examples of L-sugars include, but are not limited to, L-aldoses, L-ketoses, L-aldopentoses, L-aldohexoses, L-ketopentoses, and L-ketohexoses. L-aldopentoses include L-ribose, L-xylose, and L-lyxose. L-aldohexoses include L-allose, L-altrose, L-glucose, L-gulose, L-idose, L-galactose, and L-talose. L-ketopentoses include L-ribulose and L-xylulose. L-ketohexoses include L-fructose, L-psicose, L-sorbose and L-tagatose. Further examples of L-sugars include L-aldohexoses and L-ketohexoses. Still further examples of L-aldohexoses include L-glucose and L-gulose. Examples of L-ketohexoses include L-fructose and L-sorbose. Due to the fact that these L-hexose monosaccharides are either not metabolized by the body or they are metabolized to such a small extent by the body and colonic bacteria, they will not produce hazardous gases in the colon. A preferred L-sugar is L-glucose.

L-Glucose Monohydrate

In one particular embodiment, the L-sugar is L-glucose monohydrate.

While not wishing to be limited by theory, it has been found that the rate of dissolution of L-glucose formulations is an important parameter when formulating "ready to dissolve" colon cleansing or laxative compositions for home or medical use. Because of the greater rate of dissolution of L-glucose monohydrate relative to other reported forms of L-glucose, compositions for use as either a colon cleansing formulation or laxative can be more easily prepared by the consumer or medical professional.

The L-glucose monohydrate described herein has the empirical formula: $C_6H_{14}O_7$ or $C_6H_{12}O_6 \cdot H_2O$. The L-Glucose monohydrate comprises approximately 36.36% carbon, 7.12% hydrogen, and 56.61% oxygen; reported as C 36.36, H 7.12, O 56.51. The L-glucose monohydrate has an exact mass of 198.073953 g/mol. The L-glucose monohydrate has an average molecular weight of about 198.17115 g/mol.

In one embodiment, the L-glucose monohydrate is characterized by an X-ray powder diffraction (XRPD) pattern having one or more characteristic peaks at about 9.24, about 18.46, about 19.78, about 20.24, and about 28.36±0.2 degrees 2θ. In another embodiment, the L-glucose monohydrate exhibits peaks at two or more of the aforementioned values. In yet another embodiment, the L-glucose monohydrate exhibits peaks at three or more of the aforementioned values. In yet another embodiment, the L-glucose monohydrate exhibits peaks at four or more of the aforementioned values.

In a further embodiment, the L-glucose monohydrate is characterized by an X-ray powder diffraction (XRPD) pattern having characteristic peaks at about 9.24, about 18.46, about 19.78, about 20.24, and about 28.36±0.2 degrees 2θ.

In another embodiment, the L-glucose monohydrate is characterized by an X-ray powder diffraction (XRPD) pattern having one or more characteristic peaks at about 9.24, about 12.78, about 14.60, about 16.48, about 18.46, about 19.32, about 19.78, about 20.24, about 20.56, about 21.70, about 22.84, about 23.50, about 25.52, about 26.56, about 27.62, about 27.84, about 28.36, about 29.40, about 30.80, about 30.98, about 31.22, about 32.38, about 33.44, about 33.82, about 35.24, about 5.72, about 36.96, and about 40.18±0.2 degrees 2θ. In another embodiment, the L-glucose monohydrate exhibits peaks at two or more of the aforementioned values. In yet another embodiment, the L-glucose monohydrate exhibits peaks at three or more of the aforementioned values. In yet another embodiment, the L-glucose monohydrate exhibits peaks at four or more of the aforementioned values. In yet another embodiment, the L-glucose monohydrate exhibits peaks at five or more of the aforementioned values. In yet another embodiment, the L-glucose monohydrate exhibits peaks at six or more of the aforementioned values In another embodiment, the L-glucose monohydrate is characterized by an X-ray powder diffraction (XRPD) pattern having characteristic peaks at about 9.24, about 12.78, about 14.60, about 16.48, about 18.46, about 19.32, about 19.78, about 20.24, about 20.56, about 21.70, about 22.84, about 23.50, about 25.52, about 26.56, about 27.62, about 27.84, about 28.36, about 29.40, about 30.80, about 30.98, about 31.22, 32.38, about 33.44, about 33.82, about 35.24, about 35.72, about 36.96, and about 40.18±0.2 degrees 2.

In a further embodiment, the L-glucose monohydrate can be characterized by an X-ray powder diffraction pattern substantially as shown in FIG. 1.

With respect to the term "substantially," one skilled in the art would understand that the relative intensities of the peaks can vary, depending upon the sample preparation technique, the sample mounting procedure and the particular instrument employed. Moreover, instrument variation and other factors can affect the 2θ values. Therefore, the XRPD peak assignments can vary by plus or minus about 0.2 degrees 2θ.

The L-glucose monohydrate can be substantially free (e.g., contain 3% or less, 2% or less, 1% or less, 0.5% or less or 0.2% or less, based on the total amount of glucose by weight) or free from D-glucose and/or D-glucose monohydrate. The L-glucose monohydrate can also be substantially free or free from other impurities as other L-Sugars or D-sugars. In one embodiment, the L-glucose monohydrate is at least about 99% pure, such as at about least 99.9%, at least about 99.99% or at least about 99.999% pure, based on the total amount of sugars present.

In one embodiment, the specific optical rotation of the L-glucose monohydrate is about −52.5 to about −53.3 degrees, calculated with reference to anhydrous L-glucose. The specific optical rotation can be calculated according to the following procedure. L-Glucose monohydrate (10 g) is dissolved in de-ionized triply distilled water (80 mL). Concentrated ammonia (41 g) is diluted to a volume of 100 mL with de-ionized triply distilled water. To the solution of L-glucose monohydrate is added 0.2 mL of the diluted ammonia solution. This solution of L-glucose monohydrate and dilute ammonia is allowed to stand for 30 minutes after which time the solution is further diluted with de-ionized triply distilled water to a volume of 100 mL.

In one embodiment, the L-glucose monohydrate disclosed herein has a rate of dissolution in 100 mL of water at 25° C. of at least about 18 g/min. In a further embodiment, the rate of dissolution of L-glucose monohydrate in 100 mL of water at 25° C. is at least about 23 g/min. In another embodiment, the rate of dissolution of L-glucose monohydrate in 100 mL of water at 25° C. is at least about 26 g/min. In a yet further embodiment, the rate of dissolution of L-glucose monohydrate in 100 mL of water at 25° C. is at least about 30 g/min. In a still further embodiment, the rate of dissolution of L-glucose monohydrate in 100 mL of water at 25° C. is at least about 45.5 g/min. In a yet still further embodiment, the rate of dissolution of L-glucose monohydrate in 100 mL of water at 25° C. is at least about 60 g/min. In a yet another embodiment, the rate of dissolution of L-glucose monohydrate in 100 mL of water at 25° C. is at least about 91 g/min. However, the disclosed L-glucose monohydrate can have any rate of dissolution from at least about 18 g/min. to at least about 91 g/min. Non-limiting examples of rates include at least about 18 g/min., at least about 19 g/min., at least about 20 g/min., at least about 21 g/min., at least about 22 g/min., at least about 23 g/min., at least about 24 g/min., at least about 25 g/min., at least about 26 g/min., at least about 27 g/min., at least about 28 g/min., at least about 29 g/min., at least about 30 g/min., at least about 31 g/min., at least about 32 g/min., at least about 33 g/min., at least about 34 g/min., at least about 35 g/min., at least about 36 g/min., at least about 37 g/min., at least about 38 g/min., at least about 39 g/min., at least about 40 g/min., at least about 41 g/min., at least about 42 g/min., at least about 43 g/min., at least about 44 g/min., at least about 45 g/min., at least about 46 g/min., at least about 47 g/min., at least about 48 g/min., at least about 49 g/min., at least about 50 g/min., at least about 51 g/min., at least about 52 g/min., at least about 53 g/min., at least about 54 g/min., at least about 55 g/min., at least about 56 g/min., at least about 57 g/min., at least about 58 g/min., at least about 59 g/min., at least about 60 g/min., at least about 61 g/min., at least about 62 g/min., at least about 63 g/min., at least about 64 g/min., at least about 65 g/min., at least about 66 g/min., at least about 67 g/min., at least about 68 g/min., at least about 69 g/min., at least about 70 g/min., at least about 71 g/min., at least about 72 g/min., at least about 73 g/min., at least about 74 g/min., at least about 75 g/min., at least about 76 g/min., at least about 77 g/min., at least about 78 g/min., at least about 79 g/min., at least about 80 g/min., at least about 81 g/min., at least about 82 g/min., at least about 83 g/min., at least about 84 g/min., at least about 85 g/min., at least about 86 g/min., at least about 87 g/min., at least about 88 g/min., at least about 89 g/min., at least about 90 g/min., at least about and at least about 91 g/min. In addition, any fractional value in this range is also contemplated, for example, at least about 25.7 g/min., at least about 44.56 g/min., and at least about 73.22 g/min.

Synthesis of L-Sugars

Many L-sugars are commercially available or can be prepared by methods known in the art. See, for example, U.S. Pat. Nos. 1,830,618; 3,677,818; 4,471,114; 4,581,447; 4,718,405; 4,815,445; 4,837,315; 4,900,667; 4,939,304; 4,959,467; 4,970,302; and 5,000,794, which are all incorporated by reference herein for their teachings of L-sugar preparations.

The following procedures can be used to prepare L-glucose monohydrate from a source of L-glucose. The source can be commercial anhydrous L-glucose or the L-glucose can be obtained from a known commercial process or laboratory scale preparation. For example, a source of L-glucose can be obtained by modification of the procedure of Isbell, H. S., et al., "Synthesis of D-Glucose-1-$C^{14}$ and D-Mannose-1-$C^{14}$," *Journal of Research of the National Bureau of Standards* 48:3 pg. 163-171 (1952) include herein by reference in its entirety.

In one embodiment, the process comprises (a) adding L-glucose to water, heating the resulting mixture under reduce pressure to form a solution, and (b) cooling the resulting solution to induce crystallization, and optionally adding an organic solvent, such as ethanol.

In another embodiment, the process comprises: a) dispersing an amount from about 0.9 moles per liter to about 1.5 moles per liter of a source of L-glucose in water at a temperature of from about 55° C. to not more than about 65° C. at a reduced pressure of at least about 700 mm Hg less than atmospheric pressure, reducing the amount of water present such that the amount of water present is from about 28% to about 30% by weight of the solution, and heating the dispersion to a temperature of from about 80° C. to about 82° C. to form a solution; and b) cooling the solution to a temperature of from about 50° C. to about 55° C. to induce crystallization, further cooling the resulting slurry to a temperature of from about 25° C. to about 30° C., and adding an amount of ethanol that is from about 4.5 mL of ethanol to about 5 mL of ethanol per gram of L-glucose dispersed in step (a) to form L-glucose monohydrate.

In a further embodiment, the L-glucose monohydrate formed in step (b) is optionally isolated in a further step (c).

In one embodiment, in step (a), L-glucose is dissolved, dispersed, or suspended in water at a temperature of from about 55° C. to not more than about 65° C. under reduced pressure. The reduced pressure is at least about 700 mm Hg less than atmospheric, but can be adjusted upwards or downward depending upon the specific conditions available to the formulator. The final L-glucose concentration is from about 3.5 M to about 4 M. In one embodiment, the concentration is from about 3.77 M to about 3.89 M. In another embodiment, the concentration is from about 3.75 M to about 3.9 M.

The solution of L-glucose can be stirred or agitated under reduced pressure while heating occurs. Once the solid has been dissolved, the formulator can increase the temperature to less than about 65° C. to begin adjusting the amount of water present in the solution. The formulator, knowing the original concentration of the L-glucose, can determine the concentration of the heated solution by collecting or otherwise determining the amount of water removed under reduced pressure. The amount of water present in the solution is reduced to an amount from about 28% by weight to about 30% by weight of the solution. The resulting slurry is then heated to a temperature of from about 80° C. to about 82° C. and held until all of the L-glucose has dissolved.

Because the source of L-glucose used for this step can have larger or smaller crystal sizes, the slurry that can be heated to a temperature of from about 80° C. to about 82° C. should be stirred or agitated at that temperature range for a greater or lesser amount of time. The formulator can allow the solution to stir for a longer period of time provide the amount of water present remains in the range of from about 28% by weight to about 30% by weight of the solution.

In one embodiment of step (b), the solution resulting from step (a) is gradually cooled to a temperature of from about 50° C. to about 55° C. with continued agitation while agitation or stiffing is continued. After the solution reaches this temperature it is held there until crystallization begins. Once crystallization begins, the solution is lowered to a temperature of from about 25° C. to about 30° C. In one embodiment, the formulator can induce crystallization by adding crystals of L-glucose monohydrate. In another embodiment, the formulator can allow the solution to self nucleate.

In further embodiments, ethanol can be added to the solution to enhance crystallization. The amount of ethanol added is, for example, from about 4.5 mL of ethanol to about 5 mL of ethanol per gram of L-glucose used in step (a). For processes that introduce L-glucose as a wet mixture from a process, this amount of ethanol is calculated upon the actual mass of L-glucose entering into step (a). For example, in the case wherein anhydrous L-glucose is used as the starting material in step (a), one embodiment of the disclosed process utilizes about 4.8 mL of ethanol per gram of anhydrous L-glucose initially dissolved in step (a). The ethanol is added at any rate that allows for formation of nearly homogeneous crystals. However, the formulator can adapt the rate of addition of ethanol to any rate that is compatible with the conditions, equipment, or desired crystal size.

After allowing crystallization to occur, the solid that forms can be isolated in a further step (c). The formulator can use any means available for obtaining the crystals, for example, vacuum filtration, centrifugation, and the like. Once isolated the crystals may be washed with one-tenth the amount of ethanol used to further nucleation, for example, from about 0.45 mL of ethanol to about 0.5 mL of ethanol per gram of L-glucose used in step (a).

The obtained crystal can then be dried under a vacuum of, for example, at least about 650 mm Hg at a temperature of from about 15° C. to about 20° C., however, the formulator can adjust the vacuum and temperature to provide approximately equivalent conditions.

Compositions Containing L-Sugars

In an additional aspect, the present invention relates to compositions comprising L-sugars (such as compositions comprising L-glucose monohydrate). These compositions are preferably pharmaceutical compositions.

In one aspect, the compositions comprise: a) at least about 10% by weight of L-glucose monohydrate; and b) one or more adjunct ingredients. Compositions according to this aspect can comprise any value, for example, at least about 10%, about 20%, about 30%, about 40% up to at least about 99.999% or greater by weight of L-glucose monohydrate.

In one embodiment, the compositions comprise at least about 50% by weight of L-glucose monohydrate. In a another embodiment, the compositions comprise at least about 70% by weight of L-glucose monohydrate. In a further embodiment, the compositions comprise at least about 75% by weight of L-glucose monohydrate. In a still further embodiment, the compositions comprise at least about 80% by weight of L-glucose monohydrate. In a yet further embodiment, the compositions comprise at least about 85% by weight of L-glucose monohydrate. In a further embodiment, the compositions comprise at least about 90% by weight of L-glucose monohydrate. In another embodiment, the compositions comprise at least about 95% by weight of L-glucose monohydrate. In one embodiment, the compositions comprise at least about 99% by weight of L-glucose monohydrate, for example, at least about 99.9%, at least about 99.99% or at least about 99.999% by weight L-glucose monohydrate.

In additional non-limiting examples the compositions comprise about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9%, about 99.99% or about 99.999% by weight L-glucose monohydrate, where any of the stated values can form an upper or lower endpoint of a range. In addition, any fractional value in this range is also contemplated, for example, about 0.1%, about 4.5%, about 25.7%, about 44.56%, and about 99.98%.

The compositions described herein have an increased rate of dissolution versus anhydrous L-glucose. The compositions encompassed have a rate of dissolution in 100 mL of water at 25° C. of at least about 18 g/min. In a further embodiment, the rate of dissolution of L-glucose monohydrate containing components have a rate of solubility in 100 mL of water at 25° C. of at least about 23 g/min. In another embodiment, the rate of dissolution of L-glucose monohydrate containing components have a rate of solubility in 100 mL of water at 25° C. of at least about 26 g/min. In a yet further embodiment, the rate of dissolution of L-glucose monohydrate containing components have a rate of solubility in 100 mL of water at 25° C. of at least about 30 g/min. In a still further embodiment, the rate of dissolution of L-glucose monohydrate containing components have a rate of solubility in 100 mL of water at 25° C. of at least about 45.5 g/min. In a yet still further embodiment, the rate of dissolution of L-glucose monohydrate containing components have a rate of solubility in 100 mL of water at 25° C. of at least about 60 g/min. In a yet another embodiment, the rate of dissolution of L-glucose monohydrate containing components have a rate of solubility in 100 mL of water at 25° C. of at least about 91 g/min.

In further embodiments, compositions described herein can have any rate of dissolution from at least about 18 g/min. to at least about 91 g/min. Non-limiting examples of rates include at least about 18 g/min., at least about 19 g/min., at least about 20 g/min., at least about 21 g/min., at least about 22 g/min., at least about 23 g/min., at least about 24 g/min., at least about 25 g/min., at least about 26 g/min., at least about 27 g/min., at least about 28 g/min., at least about 29 g/min., at least about 30 g/min., at least about 31 g/min., at least about 332 g/min., at least about 33 g/min., at least about 34 g/min., at least about 35 g/min., at least about 36 g/min., at least about 37 g/min., at least about 38 g/min., at least about 39 g/min., at least about 40 g/min., at least about 41 g/min., at least about 42 g/min., at least about 43 g/min., at least about 44 g/min., at least about 45 g/min., at least about 46 g/min., at least about 47 g/min., at least about 48 g/min., at least about 49 g/min., at least about 50 g/min., at least about 51 g/min., at least about 52 g/min., at least about 53 g/min., at least about 54 g/min., at least about 55 g/min., at least about 56 g/min., at least about 57 g/min., at least about 58 g/min., at least about 59 g/min., at least about 60 g/min., at least about 61 g/min., at least about 62 g/min., at least about 63 g/min., at least about 64 g/min., at least about 65 g/min., at least about 66 g/min., at least about 67 g/min., at least about 68 g/min., at least about 69 g/min., at least about 70 g/min., at least about 71 g/min., at least about 72 g/min., at least about 73 g/min., at least about 74 g/min., at least about 75 g/min., at least about 76 g/min., at least about 77 g/min., at least about 78 g/min., at least about 79 g/min., at least about 80 g/min., at least about 81 g/min., at least about 82 g/min., at least about 83 g/min., at least about 84 g/min., at least about 85 g/min., at least about 86 g/min., at least about 87 g/min., at least about 88 g/min., at least about 89 g/min., at least about 90 g/min., at least about and at least about 91 g/min, where any of the stated values can form an upper or lower endpoint of a range. In addition, any fractional value in this range is also contemplated, for example, at least about 25.7 g/min., at least about 44.56 g/min., and at least about 73.22 g/min.

The disclosed compositions can comprise one or more adjunct ingredients. By "adjunct ingredient" is meant a chemical compound or chemical species that is not L-glucose monohydrate. In one embodiment, the adjunct ingredient is anhydrous L-glucose. In another embodiment, the adjunct ingredient is a stabilizer or material that insures the flowability of the composition. In a further embodiment, the adjunct ingredient can be any unknown impurity.

In a yet further embodiment, when the L-glucose monohydrate is prepared according to a process described herein, and depending upon the source of L-glucose used in step (a) of the process described herein, a saccharide impurity, for example, D- or L-arabinose or any of its forms, D-glucose or any of its forms, D- or L-galactose or any of its forms, D- or L-galactouronic acid or any of its forms, or any other D- or L-pentose, D- or L-hexose, and the like, can be present as an adjunct ingredient.

In a yet still further embodiment, the adjunct ingredient can be ethanol, or any other suitable processing solvent. Non-limiting examples of solvents that can be an adjunct ingredient include methanol, ethanol, propanol, iso-propanol, butanol, dioxane, pentane, iso-pentane, hexane, heptane, octane, isooctane, benzene, nitro-benzene, toluene, and xylene dichloromethane, chloroform, carbon tetrachloride, 1,1-dichloroethane, 1,2-dichloroethane, 1,1,1-trichloroethane, acetone, methyl ethyl ketone, 3-pentanone, nitromethane, tetrahydrofuran, acetonitrile, dioxane, N-methyl-2-pyrrolidone, dimethyl sulfoxide, N,N-dimethylformamide, N,N-dimethylacetamide, and hexamethylphosphoric triamide.

In a yet still another embodiment, the adjunct ingredient can be a colorant, non-limiting examples of which include FD&C Red 3, FD&C Red 40, FD&C Yellow 5, FD&C Yellow 6, FD&C Blue 1, FD&C Blue 2, FD&C Green 3, titanium dioxide, Beet Root Red, Lycopene, Carotenal, Carotenoic, Paprika Extract, Annatto, Carotenes, Caramel, Brilliant Blue FCF, Indigotine, Allura Red AC, Erythrosine, Ponceau, Carmoisine, Sunset Yellow FCF, Tartrazine, and Turmeric.

In another aspect, the composition comprises (a) at least about 10% by weight of L-glucose monohydrate; and b) anhydrous L-glucose. In further embodiments, compositions according to this aspect can comprise any value, for example, at least about 10%, about 20%, about 30%, about 40% up to at least about 99.999% by weight of L-glucose monohydrate and the corresponding balance anhydrous L-glucose.

In one embodiment, the compositions can comprise at least about 50% by weight of L-glucose monohydrate and the balance anhydrous L-glucose. In a yet a further embodiment, the compositions can comprise at least about 70% by weight of L-glucose monohydrate and the balance anhydrous L-glucose. In a still another embodiment, the compositions can comprise at least about 75% by weight of L-glucose monohydrate and the balance anhydrous L-glucose. In a still further embodiment, the compositions can comprise at least about 80% by weight of L-glucose monohydrate and the balance anhydrous L-glucose. In a yet further embodiment, the compositions can comprise at least about 85% by weight of L-glucose monohydrate and the balance anhydrous L-glucose. In a further embodiment, the compositions can comprise at least about 90% by weight of L-glucose monohydrate and the balance anhydrous L-glucose. In another embodiment, the compositions can comprise at least about 95% by weight of L-glucose monohydrate and the balance anhydrous L-glucose. In one embodiment of this aspect, the compositions can comprise at least about 99%, or at least about 99.999% by weight of L-glucose monohydrate and the balance anhydrous L-glucose.

Non-limiting examples of amounts of L-glucose monohydrate in the compositions described herein include about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9%, about 99.99% and about 99.999%, where any of the stated values can form an upper or lower endpoint of a range. In addition, any fractional value in this range is also contemplated, for example, about 0.1%, about 4.5%, about 25.7%, about 44.56%, and about 99.98%.

In certain embodiments, the compositions described herein can result from the formulator varying the procedures for preparing L-glucose monohydrate and thus forming a composition that can comprise any amount of anhydrous L-glucose. In additional embodiments, the formulator can prepare a composition that provides L-glucose monohydrate, but the composition is stored or transported in a manner that the composition reverts to a mixture of L-glucose monohydrate and anhydrous L-glucose.

In one embodiment, the amount of anhydrous L-glucose present in the composition is not primary to the performance (i.e., the rate of dissolution of the composition) due to one or more factors. For example, the final concentration of an aqueous solution of the composition is such that the rate of dissolution of the anhydrous L-glucose is not a limiting factor. An example of this is the circumstance wherein the mixture of L-glucose monohydrate and anhydrous L-glucose is formulated with a material that has a higher rate of dissolution. In some instances, the mixture can be formulated with another ingredient that has greater heat of solution, i.e., $\Delta H > 19$ kJ/mol, thereby requiring warming of the admixture.

In another aspect, disclosed are compositions for use in colonic cleansing, comprising: a) from about 0.01% to about 99.99% by weight of an active component, comprising: i) from about 0.001% to about 99.999% by weight of L-glucose monohydrate; and ii) from about 0.001% to about 99.999% by weight of anhydrous L-glucose; and b) the balance adjunct ingredients.

A further embodiment of this aspect relates to a composition for use as a laxative, comprising: a) from about 0.01% to about 99.99% by weight of an active component, comprising: i) from about 0.001% to about 99.999% by weight of L-glucose monohydrate; and ii) from about 0.001% to about 99.999% by weight of anhydrous L-glucose; and b) the balance adjunct ingredients.

By "active component" as it relates to this aspect is meant that the adjunct ingredients are not known or understood to have colon cleansing or laxative activity. As such, the adjunct ingredients can be stabilizers, colorants, flavorants, and the like.

In addition to having a rapid rate of dissolution in water, the disclosed compositions have a high solubility in water, for example, a solubility in water of from about 0.85 g/mL to about 1.5 g/mL at 25° C. In another embodiment, the compositions have a solubility in water of from about 0.9 g/mL to about 1.2 g/mL at 25° C. In a further embodiment, the compositions have a solubility in water of from about 0.92 g/mL to about 0.98 g/mL at 25° C. In a yet further embodiment, the compositions have a solubility in water of from about 0.91 g/mL to about 0.93 g/mL at 25° C.

A further embodiment of the disclosed compositions relates pharmaceutical compositions, comprising: a) from about 0.01% to about 99.99% by weight of a non-absorbable saccharide component, comprising: i) from about 0.001% to about 99.999% by weight of L-glucose monohydrate; and ii) from about 0.001% to about 50% by weight of anhydrous L-glucose; and b) one or more pharmaceutically active ingredients.

By "non-absorbable saccharide component" is meant compounds that are not readily absorbed by the body, for example, L-glucose or compounds that are sweet to the taste, but because of their high sweetness index, do not add bulk or mass to the composition and thus to not interfere with the colon cleansing embodiments. As such, although L-glucose is understood not to be absorbed, the formulator can include other ingredients that have the desirable organoleptic property of sweetness, but which are not absorbed or that are minimally absorbed by the body or which are recognized as non-caloric sweeteners. Non-limiting examples of non-caloric sweeteners include acesulfame and salts thereof, aspartame, neotame, saccharin, sucralose, stevia, and tagatose. In addition, other non-absorbable sugars include xylitol and the like.

The compositions may further include one or more pharmaceutically active ingredients. By "pharmaceutically active ingredient" is meant a substance that provides a medical benefit to the consumer but does not affect the colonic cleansing or laxative properties of the composition. For example, the pharmaceutically active ingredient can be a substance that relieves anxiety. In addition, the active ingredient can counteract any stomach or esophageal reaction due to fasting.

In one embodiment, the compositions comprise: i) from about 10% to about 90% by weight of L-glucose monohydrate; and ii) from about 10% to about 50% by weight of anhydrous L-glucose.

In another embodiment, the compositions comprise: i) from about 20% to about 80% by weight of L-glucose monohydrate; and ii) from about 20% to about 50% by weight of anhydrous L-glucose.

In a further embodiment, the compositions comprise: i) from about 30% to about 70% by weight of L-glucose monohydrate; and ii) from about 30% to about 50% by weight of anhydrous L-glucose.

In a still further embodiment, the compositions comprise: i) from about 40% to about 60% by weight of L-glucose monohydrate; and ii) from about 40% to about 50% by weight of anhydrous L-glucose.

In a yet further embodiment, the compositions comprise: i) about 50% by weight of L-glucose monohydrate; and ii) about 50% by weight of anhydrous L-glucose monohydrate In one embodiment, the compositions can comprise from about 10% to about 90% by weight of the pharmaceutically active component(s). In a further embodiment, the compositions of this aspect can comprise from about 10% to about 90% by weight of the pharmaceutically active component(s). In another embodiment, the compositions of this aspect can comprise from about 20% to about 90% by weight of the pharmaceutically active component(s). In a further embodiment, the compositions of this aspect can comprise from about 30% to about 90% by weight of the pharmaceutically active component(s). In a yet further embodiment, the compositions of this aspect can comprise from about 10% to about 80% by weight of the pharmaceutically active component(s). In a still further embodiment, the compositions of this aspect can comprise from about 10% to about 70% by weight of the pharmaceutically active component(s).

In various embodiments, the L-glucose monohydrate is used in a pharmaceutical composition, for example a composition for use in colon cleansing. For example, a colonic cleansing method can comprise orally administering to a subject in one or more doses a composition comprising an amount of one or more L-sugars that is greater than about 48 g, wherein one of the L-sugars is L-glucose monohydrate, or wherein the L-sugars consist solely of L-glucose monohydrate.

The compositions for colonic cleansing can include the L-sugar in a composition, such as a food product. For example, a colonic cleansing composition in the form of a gel can include combining water, L-sugar and a gelling agent. Gelling agents include, for example, gelatin, such as Gelatin, Type A, 25 Bloom, 50 mesh, from Great Lakes Gelatin, PO Box 917, Grayslake, Ill.; agar such as Sigma brand Agar A-7002 Lot 71K0093; and commercially available products that include flavorings, such as JELL-O™ brand desert mix; and the like. In one aspect, about 85 g of JELL-O™ can be boiled in about 130 mL of water and combined with a near boiling mixture containing 45 mL of L-sugar diluted with about 65 mL of water and the flavoring. Incorporation of a laxative agent into a gel is described, for example, in US Publication No. 2004/0071779 A1, which is incorporated by reference herein in its entirety.

A composition for colonic cleansing and/or a kit for colonic cleansing, as disclosed herein, comprises an L-sugar. The composition and/or kit can also include one or more other ingredients, such as flavorings, colorants, and/or dispersants. The L-sugar can be in the form of, for example, a solution, a suspension, a colloid, a dispersion, a slurry or a gel. A composition for colonic cleansing can include the L-sugar in solid form, including a powdered solid, a granulated solid, or one or more tablets. When present as a solid, the L-sugar can be anhydrous, or can be present as a hydrate (e.g., monohydrate), for example L-glucose monohydrate; all amounts of L-sugars and L-glucose referred to herein exclude water of hydration and any other compounds that can be present in the specific form of L-sugar used. The L-sugar can be in one or more containers, such as bottles, tubs, sachets, envelopes, packets, tubes and ampoules.

In certain aspects, the L-sugar is dissolved in water (or other comestible liquid). The rate of dissolution is directly proportional to surface area of the solute. Thus, it can be advantageous to use very fine powders of the anhydrous form of L-sugars since they have large surface areas. Thus, when a subject adds water to the anhydrous L-sugar and stirs for a few minutes, the material will dissolve. If, however, a subject does not sufficiently stir, the solids can clump and dissolution rate can become quite slow.

While not wishing to be bound by theory, it is believed that the reason for this phenomenon is allowance for local supersaturation of L-glucose in water to occur near the crystals from which dissolution is occurring. This results in the rapid growth and deposition of L-glucose monohydrate crystals onto the anhydrous material, and a dramatic reduction of the overall surface area upon which dissolution rate depends.

The advantage of L-glucose monohydrate (or similarly the monohydrate of other L-sugars) is that there is no longer a transition of crystal forms affecting the overall surface area. If one begins with high surface area of L-glucose monohydrate, they can add water and apply even minimal stiffing to accomplish rapid dissolution (e.g., within 1 minute or so). As such, in certain embodiments herein the L-sugar that is provided in the kits is in the monohydrate form.

Kits Containing L-Sugars

In an additional aspect, the present invention relates to kits comprising L-sugars (such as compositions comprising L-glucose monohydrate). In one embodiment, the kit comprises a package and an amount of an L-sugar (e.g., L-glucose monohydrate) effective for colon cleansing, in the package.

In a further embodiment, the kit comprises at least two separate pre-measured doses of L-sugar, such as a first dose and a second dose, preferably in separate containers. In some examples, the kit can include two containers of L-sugar, each container having an amount of L-sugar appropriate to combine with water, to form an orally administrable first or second dose. In a further example, the L-sugar can be present as a powder contained in two packets, the packets corresponding to a first and second dose of colon cleansing agent. In a still further example, the kit can comprise a container containing a pre-measured amount of L-sugar into which water can be added to dissolve the L-sugar to the desired volume. A kit can contain one, two, or more such containers. The disclosed kits can also comprise instructions for colonoscopy preparation.

In certain embodiments, the total amount of L-sugar in the kit is greater than 48 g. In further embodiments, the total amount of L-sugar in the kit is from greater than about 48 g to about 200 g.

In another embodiment, the first dose in the kit comprises at least 36 g L-sugar and the second dose comprises at least 30 g L-sugar. For example, the first does in the kit comprises from about 36 g to about 80 g L-sugar and the second dose comprises from about 30 g to about 80 g L-sugar.

In one embodiment the L-sugar is L-glucose. In another embodiment, the L-sugar is L-glucose monohydrate.

One or more anorectal wipes optionally can be present in the kit. Anorectal wipes can be made from any suitable substrate, such as cloth, paper, or combinations thereof, and can be wetted with an aqueous mixture that can include one or more active ingredients. Examples of active ingredients include a local anesthetic such as pramoxine hydrochloride, and a protectant such as glycerin. The aqueous mixture also can include one or more inactive ingredients, such as cetylpyridinium chloride, citric acid, disodium EDTA, eucalyptol, menthol, octoxynol-9, sodium benzoate, and sodium citrate. The anorectal wipes can be in the form of pads and the like, such as FLEE™ Pain-Relief Pre-Moistened anorectal pads. In one aspect, four individually wrapped wipes are preferred. The anorectal wipes can be rectangular in shape, having dimensions of about 4 cm by about 7 cm. The anorectal wipes can be present in the kit in one or more containers, such as bottles, tubs, sachets, envelopes, packets, tubes, and the like. For example, the kit can include two packets containing one or more anorectal wipes each. In one embodiment, the kit includes at least two anorectal wipes packets, each packet containing two anorectal wipes.

Methods of Treatment

In preclinical studies, there was no metabolism of L-glucose in any mammalian species studied. In mice, rats, dogs, rabbits, and monkeys, the major route of L-glucose elimination was urinary excretion. Food restriction had no significant effect on the metabolism of L-glucose. A dietary study in Sprague-Dawley rats showed that there was no overt evidence of toxicity from the continuous administration of L-glucose for 90 days. The maximum tolerated dose in rats was determined to be 10% dietary level of L-glucose.

Clinical studies have shown that L-glucose is moderately absorbed from the human intestine. Breath hydrogen results in humans were comparable with results obtained from in vitro studies, indicating that colonic bacteria do not metabolize L-glucose. The major routes of elimination of L-glucose in humans are fecal and urinary excretion. No significant glucose or insulin response was noted after the administration of L-glucose. Mild upper gastrointestinal symptoms such as vomiting, nausea, belching/rifting, and bloating occurred in a minority of subjects. Lower gastrointestinal symptoms, such as cramping and gas/flatus, occurred in a majority of subjects, but symptoms were mild and did not interfere with their daily activities. Subjects reported that the taste of L-glucose was generally perceived as pleasant.

Despite these generally advantageous properties of L-sugars, they have not been found to be satisfactory as a colonic cleansing agent in various tests. For example, an open-label, historically controlled, single-dose study of a 24-g dose of L-glucose was conducted to determine the safety and effectiveness of L-glucose as a colon-cleansing agent before colonoscopy (Raymer et al., "An open-label trial of L-glucose as a colon-cleansing agent before colonoscopy," *Gastrointest Endosc* 58(1):30-5, 2003). Based on the results of the colonoscopies, the majority of subjects (80%) had a colonoscopy preparation grade of "excellent" or "good." However, the 80% success rating reported was less than that observed with conventional PEG compositions, which in turn are less effective than colonic cleansing agents based on phosphate salts (Hsu et al., "Meta-analysis and cost comparison of polyethylene glycol lavage versus sodium phosphate for colonoscopy preparation," *Gastrointestinal Endoscopy* 48(3):276-282, 1998). It is further noted that the reported 80% success rating is equivalent to a 20% failure rating, which is not acceptable, especially when one considers that each failed colonoscopy possibly means a missed diagnosis, not to mention great expense and inconvenience to the doctor and patient when rescheduling the colonoscopy.

The methods disclosed herein use compositions comprising L-sugars in doses that produce significantly improved colonic cleansing.

In one embodiment, disclosed herein are methods for colonic cleansing that comprise orally administering to a subject in one or more doses (e.g., within a 24 hour period) a composition comprising an amount of an L-sugar that is greater than about 48 g. For example, an L-sugar can be administered in an amount from greater than about 48 g to about 200 g of the L-sugar, from about 50 g to about 150 g of the L-sugar, from about 60 g to about 140 g of the L-sugar, from about 70 g to about 130 g of the L-sugar, from about 80 g to about 120 g of the L-sugar, or from about 90 g to about 110 g of the L-sugar.

In other examples, an L-sugar can be administered in an amount of about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, or about 200 g of the L-sugar, where any of the stated values can form an upper or lower endpoint of a dosage range.

Also disclosed herein are methods for colonic cleansing that comprise administering a first dose of a composition comprising an L-sugar and then a second dose of a composition comprising an L-sugar. For example, one can administer a first dose comprising at least about 36 g of the L-sugar and a second dose comprising at least about 30 g of the L-sugar, a first dose comprising from about 36 g to about 80 g of the L-sugar and a second dose comprising from about 30 g to about 80 g of the L-sugar, a first dose comprising from about 40 g to about 60 g of the L-sugar and a second dose comprising from about 40 g to about 60 g of the L-sugar, a first dose comprising from about 45 g to about 55 g of the L-sugar and a second dose comprising from about 45 g to about 55 g of the L-sugar, a first dose comprising from about 40 g to about 50 g of the L-sugar and a second dose comprising from about 30 g to about 40 g of the L-sugar, or a first dose comprising at least about 48 g of the L-sugar and a second dose comprising at least about 48 g of the L-sugar.

In certain embodiments, the second dose is administered at least about 2, about 4, about 6, about 8, about 10, or about 12 hours after the first dose.

In certain embodiments of the methods described herein, the L-sugar is L-glucose. In other embodiments of the methods described herein, the L-sugar is L-glucose monohydrate.

In one embodiment, the methods described herein include administering a first dose comprising about 48 g L-glucose (which is equivalent to about 52.8 g L-glucose monohydrate) and a second dose comprising about 48 g L-glucose (or about 52.8 g L-glucose monohydrate). Preferably, the first and second doses are aqueous solutions of the L-glucose.

In one embodiment, the present invention relates to a method for colon cleansing in a subject undergoing a colonoscopy, that includes administering to the subject an aqueous solution containing about 52.8 g L-glucose monohydrate (which is equivalent to about 48 g of active L-glucose) the night before the colonoscopy, and administering to the subject an aqueous solution containing about 52.8 g L-glucose monohydrate the morning of, but prior to, the colonoscopy.

In further embodiments, each dose of L-glucose monohydrate is dissolved in 8 ounces of water prior to administration to the subject.

In one embodiment, the first dose of L-glucose monohydrate is administered at about 6 pm the night before the colonoscopy. In another embodiment, the second dose of L-glucose monohydrate is administered at about 6 am the day of the colonoscopy. In a further embodiment, the first dose of L-glucose monohydrate is administered at about 6 pm the night before the colonoscopy and the second dose of L-glucose monohydrate is administered at about 6 am the day of the colonoscopy.

In additional embodiments, administration of a composition comprising an L-sugar can be accomplished by dissolving the composition comprising the L-sugar in water (or other comestible) and administering orally. Alternatively, tablet(s), capsule(s), sachets, powders, granules, suspensions, emulsions, or solutions in water or non-aqueous media can be ingested by or administered to a subject. Thickeners, flavorings, diluents, emulsifiers, dispersing aids or binders can be used. The disclosed compositions can also be administered by enema.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Preparation of L-Glucose Monohydrate

L-glucose (144 kg, 800 mol) is dissolved in water (600 L) in a sealed vessel and the pressure reduced by approximately 700 mm Hg. The solution is heated to less than about 65° C. and the water content reduced to about 28% to about 30% by weight. The solution is then heated to a temperature from about 80° C. to about 82° C. and held until the observed solids are dissolved. The solution is then gradually cooled and held at a temperature of from about 50° C. to about 55° C. until crystallization occurs. Once crystallization is initiated the solution is further cooled to a temperature of from about 25° C. to about 30° C. with continued agitation. Crystallization is allowed to continue for about 12 hours. Ethanol (700 L) that has been denatured with isopropanol, is added over approximately 30 minutes.

After about 90 minutes, the resulting crystal slurry is centrifuged and the solid is collected, washed with denatured ethanol (70 L) and transferred to a tray drier. The crystals are dried under a vacuum of at least about 650 mm Hg at a temperature from about 15° C. to about 20° C. to afford 110 kg (69.4% yield) of L-glucose monohydrate. Karl Fischer water analysis of final product found that there was approximately 9% water present, thereby affirming L-glucose monohydrate. The remaining L-glucose can be recycled to obtain additional L-glucose monohydrate

L-Glucose Monohydrate Composition Examples

The following are non-limiting exemplary compositions containing L-glucose monohydrate. The following are solid compositions that are dissolved in 100 mL to make up a colon cleansing and/or laxative composition. The following amounts are in grams.

Composition Examples 1-5

| Ingredients | 1 | 2 | 3 | 4 | 5 |
|---|---|---|---|---|---|
| L-glucose monohydrate | 48 | 48 | 48 | 48 | 48 |
| anhydrous L-glucose | — | 0.05 | 0.075 | 0.1 | 0.125 |

Composition Examples 6-10

| Ingredients | 6 | 7 | 8 | 9 | 10 |
|---|---|---|---|---|---|
| L-glucose monohydrate | 50 | 50 | 50 | 50 | 50 |
| anhydrous L-glucose | — | 0.05 | 0.075 | 0.1 | 0.125 |

Composition Examples 11-15

| Ingredients | 11 | 12 | 13 | 14 | 15 |
|---|---|---|---|---|---|
| L-glucose monohydrate | 60 | 60 | 60 | 60 | 60 |
| anhydrous L-glucose | — | 0.075 | 0.1 | 0.125 | 0.15 |

Composition Examples 16-20

| Ingredients | 16 | 17 | 18 | 19 | 20 |
|---|---|---|---|---|---|
| L-glucose monohydrate | 70 | 70 | 70 | 70 | 70 |
| anhydrous L-glucose | — | 0.075 | 0.1 | 0.125 | 0.15 |

Composition Examples 21-25

| Ingredients | 21 | 22 | 23 | 24 | 25 |
|---|---|---|---|---|---|
| L-glucose monohydrate | 80 | 80 | 80 | 80 | 80 |
| anhydrous L-glucose | — | 0.1 | 0.125 | 0.15 | 0.175 |

Composition Examples 26-30

| Ingredients | 26 | 27 | 28 | 29 | 30 |
|---|---|---|---|---|---|
| L-glucose monohydrate | 90 | 90 | 90 | 90 | 90 |
| anhydrous L-glucose | — | 0.1 | 0.125 | 0.15 | 0.175 |

The L-glucose monohydrate can have a rate of solubility that increases with increasing temperature. As such, compositions comprising L-glucose monohydrate can be warmed by the user to increase the rate of dissolution.

The following describes methods for determining the increased dissolution rate of L-glucose monohydrate comprising compositions.

To separate 600 mL beakers is charged L-glucose monohydrate (53 g) and anhydrous L-glucose (48 g). Each sample comprises approximately an equivalent amount of L-glucose on a weight basis. Carefully, to avoid agitation and mixing, doubly distilled water (240 mL) is added to each beaker. In one example, the solution is stirred immediately after addition of water. In a second example, the solutions are allowed to stand for 5 minutes before agitation. The stiffing was conducted in a manner duplicating the way a consumer is expected to stir a sample prior to use. The following Table summaries these experiments which were conducted in duplicate.

Because of the increased rate of dissolution of L-glucose monohydrate, it can be used for formulations wherein rapid dissolution of the composition ingredients is desired. For example, the L-glucose monohydrate can be formulated into a composition that is taken orally for colonic cleansing. The composition can be used by the consumer or by medical personnel. The composition for colonic cleansing can include the L-glucose monohydrate in solid form, including a powdered solid, a granulated solid, or one or more tablets. When present as a solid, the L-glucose monohydrate can be in one or more containers, such as bottles, tubs, sachets, envelopes, packets, tubes and ampoules Bowel Preparation Scales The American Society for Gastrointestinal Endoscopy (ASGE) and the American College of Gastroenterology Taskforce on Quality in Endoscopy have published guidelines for procedural documentation that include a recommendation to assess bowel cleansing quality in all colonoscopy reports (Rex et al. "Quality indicators for colonoscopy," *Am J Gastroenterol* 101:873-85, 2006). Unfortunately, there is no industry-wide standard for assessing the adequacy of bowel preparation for colonoscopy. Previously published scales differ significantly in their design (global vs. segmental), scoring system (categorical vs. numerical), and application (before or after washing and cleansing). Advantages and disadvantages of each scoring method are shown in Table 1.

| Sample | Time[4] | Observations |
|---|---|---|
| L-glucose monohydrate[1] | No delay | Sample fully dissolved after 2.5 min. of stirring. Several clusters of solid at 1 min. Final solution was clear, colorless and homogeneous |
| L-glucose monohydrate[1] | 5 min. delay | Sample fully dissolved after 2.5 min. of stirring. Several clusters of solid at 1 min. Final solution was clear, colorless and homogeneous |
| L-glucose monohydrate[2] | No delay | Fully dissolved after 2 min. of stirring. Final solution was clear, colorless and homogeneous |
| L-glucose monohydrate[2] | 5 min. delay | Fully dissolved after 1 min. of stirring. Final solution was clear, colorless and homogeneous |
| anhydrous L-glucose[3] | No delay | Most of the sample dissolved after 5 min. of stirring. Clear solution results with latent insoluble particles present. |
| anhydrous L-glucose[3] | 5 min. delay | Material clumped into a hard mass during time delay. Most of the sample dissolved after 8 min. of stirring. Clear solution results with latent insoluble particles present. |

[1] Sample obtained from Danisco Inc., Lot # Mil-S5-110408A.
[2] Sample obtained from Arch Pharmalabs Lmtd., Lot # VLLGC-017090001.
[3] Sample obtained from Danisco Inc., Lot # Del-S5-190208A.
[4] Samples with no delay are immediately stirred in a manner consistent with the practice of consumers, i.e., use of a spoon or stirring stick. Samples with a time delay are not agitated until the end of the time delay.

TABLE 1

Theoretical advantages and disadvantages of bowel preparation scoring systems

| | Advantages | Disadvantages |
|---|---|---|
| Design | | |
| Global | Easy to use<br>Easy to understand | Difficult to account for segmental differences in cleansing |
| Segmental | Accounts for segmental differences in cleansing quality that occur with all preps<br>Permits independent study of right colon cleansing, a postulated factor in missed colon cancers | More complex<br>Challenging to validate by videotape review if segments aren't designated |
| Scoring System | | |
| Categorical | Easy to understand<br>Standard language of "Excellent + Good" generally considered successful prep in literature | Varying definitions of "Excellent", "Good", "Fair", and "Poor" prohibit cross-trial comparisons |
| Numerical | Easy to statistically analyze | Non-descriptive<br>Requires an arbitrary numerical threshold to determine adequacy or inadequacy<br>Small but statistically significant differences in numerical score might not be clinically significant |
| Application | | |
| Before Washing/Suctioning | Reflects true cathartic effects of bowel preparation | Fails to account for ease of clearing residual fluid or feces |
| After Washing/Suctioning | Reflects ability of colonoscopist to view the colonic mucosa, a critical endpoint | Does not account for time spent in clearing colon, a significant efficiency factor |

Historically, bowel preparation manufacturers have relied upon their own, unique scales to assess the adequacy of bowel cleansing in head-to-head clinical trials. These scales differ widely in their designs, making cross-trial comparisons impossible. Further, the lack of reliable, validated definitions of categorical descriptions of bowel cleansing (i.e. "Excellent", "Good", "Fair", and "Poor") renders any guideline for the documentation of bowel preparation adequacy impractical to implement.

Applicants have relied upon a combination of a categorical, 4-point scale and a numerical, segmental scoring system to assess bowel cleansing quality (Balaban et al. "Low volume bowel preparation for colonoscopy: randomized, endoscopist-blinded trial of liquid sodium phosphate versus tablet sodium phosphate," *Am J Gastroenterol* 98:827-32, 2003). The basic 4-point scale, known as the Global Preparation Assessment (GPA), is essentially the same as the original scale used in the first randomized controlled trial of PHOSPHO-SODA™ as a bowel cleansing agent published in 1990 by Vanner, et al. ("A randomized prospective trial comparing oral sodium phosphate with standard polyethylene glycol-based lavage solution (Golytely) in the preparation of patients for colonoscopy," *Am J Gastroenterol* 85:422-7, 1990). The numerical scoring system, known as the Residual Stool Score (RSS), is a continuously variable, averaged segmental scoring instrument that assesses both the amount and consistency of residual stool before suctioning (a measure of the cathartic activity of the bowel cleansing regimen) as well as the percent of the bowel wall seen after washing and cleansing (a measure of the ultimate endpoint for bowel preparation success). The two scales are shown below.

Global Preparation Assessment
  Excellent=clean colon or small volume of clear liquid
  Good=moderate to large volume of clear to semiclear liquid
  Fair=some semisolid stool suctioned or washed away
  Poor=semisolid or solid stool unable to be suctioned or washed away Residual Stool Score
  Effectiveness variables include assessment of the amount and consistency of stool in the bowel and the percent bowel wall visualized. Segmental evaluations are done at the level of the rectum, descending colon, transverse colon, ascending colon, and cecum according to the scales below.

| Stool Amount: | Stool Consistency: | Percent Wall Visualized: |
|---|---|---|
| 0 = None | 0 = None | 0 = >95% |
| 1 = Minimal | 1 = Clear yellow liquid | 1 = 85% to 94% |
| 2 = Small | 2 = Muddy liquid | 2 = 75% to 84% |
| 3 = Moderate | 3 = Particulate stool | 3 = 50% to 74% |
| 4 = Large | 4 = Solid stool | 4 = <50% |

Amount of stool and stool consistency is scored before washing and suctioning, while percent bowel wall visualized is scored after washing and suctioning. The sum of the three ratings constitutes the score for each segment. The final RSS is determined by calculating a mean of the scores for all segments seen. If the colonoscopy does not proceed through the five sections of the colon, the segment where the colonoscopy ended and the reason for stopping is noted, and the segments are rated as viewed up to that point.

The GPA scale includes representative colonoscopic images of each cleansing grade as a visual aid. The 4-point GPA has been demonstrated to have a high degree of statistical correlation with the segmental RSS ($r=-0.76$, $p<0.001$) (Balaban et al. *Am J Gastroenterol* 98:827-32, 2003).

The bowel preparation assessments described in the Examples below employed two scales to describe the amount and consistency of residual stool as well as the ability of the endoscopist to clear the stool for complete examination. Certain elements of the scoring method were completed before suctioning and washing and reflected the ability of the bowel preparation to provide a dry and clean prep, which is advantageous to minimize time of additional lavage and suctioning during the exam. The other elements were completed after suctioning and washing and reflected the ability to completely examine the colon.

Other published bowel preparation scales focus either exclusively on visualization of the colon or on a description of residual stool, but do not permit independent assessment of each of these elements. Furthermore, the absence of a segmental component in some scales precludes important evaluations of the relative efficacy of cleansing in the right and left colon, a consideration for endoscopists.

Incremental modifications of the language of the GPA and RSS scales from dozens of researchers over the past 7 years has resulted in descriptions that are free of the ambiguity that hampers the utility of other scales. As an example, the scale employed by Raymer et al. includes a description of "small bits of adherent fecal fluid" in the Excellent category; it is not clear whether "bits" refers to a solid component, as one might expect, or a liquid component, which is described by "fluid." Of note, solid feces are not permissible in either the Excellent or Good scores used in the examples below, which indicates that the scale used in the examples below is more rigorous.

Applicant's method for bowel cleansing assessment, including the Global Preparation Assessment and the Residual Stool Score, addresses unique and complementary elements of bowel cleansing for colonoscopy. By using both scales, the method permits a complete analysis of fecal clearance, including the ease with which complete colonoscopic exam can be achieved. Compared to other published scoring systems, Applicant's method is more rigorous in its language and more complete in its description of bowel preparation adequacy.

Comparative Example 1

A multicenter, double-blind, dose-range-finding study to evaluate the effectiveness and safety of L-glucose as a colon-cleansing agent before colonoscopy was conducted. Doses used in this study were 12 g, 16 g, 20 g, and 24 g. The assessment of the preparations was based on the scale used in Hsu et al., "Meta-analysis and cost comparison of polyethylene glycol lavage versus sodium phosphate for colonoscopy preparation," *Gastrointestinal Endoscopy* 48(3):276-282, 1998, wherein small bits of fecal material in the colon were allowed in an "Excellent" score. Thus, the 24 g dose experiments were similar to the highest dose experiments of Raymer et al. The results indicated that L-glucose in single doses within these ranges was not acceptable as a colonic cleanser.

Comparative Example 2

A randomized, single-blind study designed to determine the clinical effectiveness of L-glucose as a bowel preparation before colonoscopy was performed. Three dose regimens were evaluated: 24 g in the evening only, 30 g in the evening only, and 24 g in the evening followed by 12 g in the morning (36 g total). Here, Applicant's GPA scale described herein was used to evaluate the preparations. In this study, the 2 evening-only doses (24 g and 30 g) were suspended for lack of effectiveness. This study showed that L-glucose given as a split dose had greater clinical effectiveness of bowel cleansing. In fact, the split dose schedule was statistically superior to the single dose schedule: GPA showed a significant difference in efficacy ($p<0.001$) between a split-dose as compared to the single-dose schedule. Clinical efficacy (defined as a combination of "excellent" and "good" assessments) for the split-dose schedule was 19/27 (70%), as compared to 7/31 (23%) in the single-dose schedule ($p<0.001$). Commonly reported adverse events were generally absent or mild, and there were no clinically significant changes in laboratory test results. Nearly all subjects reported the L-glucose cleansing solution as easy and convenient to use. The taste was favorably rated as very pleasant to somewhat pleasant. Overall tolerance to the bowel preparation was rated as good or very good and most subjects reported they were willing to repeat the regimen.

As noted above in the description of Applicant's GPA scale, the criteria for determining whether a preparation was deemed "excellent" or "good" was respectively defined as "clean colon or small volume of clear liquid" or "moderate to large volume of clear to semi-clear liquid." These criteria are more stringent than the rating system used by Raymer et al. discussed supra since Raymer's "excellent" and "good" ratings were respectively defined as "no more than small bits of adherent fecal fluid" and "small amounts of feces or fluid not interfering with the examination." Thus, Raymer's "excellent" rating would likely not qualify as even a "good" rating in Applicant's GPA scale.

Example 3

This open-label, 2-site study employed a dose-escalating design using 3 split doses of L-glucose (24 g/24 g, 36 g/36 g, and 48 g/48 g). The doses were administered the night before and the morning of a scheduled colonoscopy. The study was conducted in Phase I facilities to control for administration of L-glucose and adherence to the dietary and hydration regimen.

Three dose cohorts of 24 subjects were evenly divided between males and females for each cohort. Subjects who were scheduled to undergo an elective colonoscopy, who met the study entrance criteria, and who gave their consent to participate in the study were enrolled. Study subjects who met the inclusion criteria and did not meet the exclusion criteria were enrolled into the lowest dose cohort first. Each subject observed a strict diet and hydration regimen as part of the study medication administration.

The site pharmacist prepared the L-glucose preparation based on the study medication preparation manual provided. Each subject, regardless of dose cohort, received the dose in 8 ounces of water, which was to be consumed within a 10-minute period. Dose cohorts proceeded in a dose-escalating fashion starting with the lowest dose (24 g/24 g) and escalated according to a dose escalation decision tree.

The physician performing the colonoscopy utilized Applicant's GPA scale to evaluate the quality of bowel preparation as before suctioning and washing. If the colonoscopy did not proceed through the colon to the cecum for anatomical or medical reasons, and not because of retained stool, the location where the colonoscopy ended was noted and the preparation was rated as viewed up to that point. When the colonoscopy did not proceed through the colon to the cecum for reasons of inadequate bowel preparation, because of the presence of retained stool, the GPA was rated as "poor."

The Residual Stool Score (RSS) described above was also used to assess bowel cleansing in each of the 5 segments of the bowel (rectum, descending colon, transverse colon, ascending colon, and cecum). As noted, assessments included the amount of stool present, the consistency of the stool, and the estimated percentage of the bowel wall visualized in each segment.

For reasons of inadequate bowel preparation, sections of the bowel that were not directly examined during colonoscopy were rated as "poor" on all three measures listed previously.

A total of 24 subjects were enrolled into each of the three dose cohorts. All 72 subjects were included in the intent-to-treat (ITT) and safety populations.

There were 23 (95.8%) subjects in each dose cohort who had a complete colonoscopy (endoscopist was able to reach to the level of the cecum). The mean (SD) of GPAs were 3.29 (0.81) for the 24 g/24 g dose cohort, 3.42 (0.83) for the 36 g/36 g dose cohort, and 3.88 (0.45) for the 48 g/48 g dose cohort. The GPA scores were rated "excellent" for at least half of the subjects in each of the 3 dose cohorts including 12 (50.0%) subjects in the 24 g/24 g dose cohort, 14 (58.3%) subjects in the 36 g/36 g dose cohort, and 22 (91.7%) subjects in the 48 g/48 g dose cohort. Only 1 (4.2%) subject in the 36 g/36 g dose cohort had a GPA score that was rated "poor." Table 2 summarizes the GPA results.

TABLE 2

Summary of Global Preparation Assessment by Dose Cohort (Intent-to-Treat Population)

| Global Preparation Assessment | 24 g/24 g Cohort (n = 24) | 36 g/36 g Cohort (n = 24) | 48 g/48 g Cohort (n = 24) | Total (N = 72) |
|---|---|---|---|---|
| N | 24 | 24 | 24 | 72 |
| Mean (SD) | 3.29 (0.81) | 3.42 (0.83) | 3.88 (0.45) | 3.53 (0.75) |
| Median | 3.50 | 4.00 | 4.00 | 4.00 |
| Min, Max | 2.00, 4.00 | 1.00, 4.00 | 2.00, 4.00 | 1.00, 4.00 |
| Excellent | 12 (50.0) | 14 (58.3) | 22 (91.7) | 48 (66.7) |
| Good | 7 (29.2) | 7 (29.2) | 1 (4.2) | 15 (20.8) |
| Fair | 5 (20.8) | 2 (8.3) | 1 (4.2) | 8 (11.1) |
| Poor | 0 (0.0) | 1 (4.2) | 0 (0.0) | 1 (1.4) |

SD = standard deviation, Min = minimum, Max = maximum.
Note:
Percentages are based on the number of subjects in each dose cohort.

There were 30 (96.8%) subjects at Site 01 and 39 (95.1%) subjects at Site 02 who had a complete colonoscopy. The mean (SD) GPA was 3.68 (0.75) for Site 01 and 3.41 (0.74) for Site 02. The GPA scores were rated "excellent" for more than half of the subjects at Site 01 (25 subjects, 80.7%) and Site 02 (23 subjects, 56.1%). Only 1 (3.2%) subject at Site 01 had a GPA score that was rated "poor."

The results of the efficacy analysis demonstrated the following. The GPA scores were rated "excellent" for at least half of the subjects in all 3 dose cohorts including 12 (50.0%) subjects in the 24 g/24 g dose cohort, 14 (58.3%) subjects in the 36 g/36 g dose cohort, and 22 (91.7%) subjects in the 48 g/48 g dose cohort. There were 23 (95.8%) subjects in each dose cohort who had a complete colonoscopy. The dose that achieved the greatest efficacy was the 48 g/48 g dose, based on the high percentage of "excellent" examinations observed at both sites, supported by the shortest time to the first watery bowel movement. Further, the 48 g/48 g dose provided a more robust bowel cleansing, based on the higher percentage of "excellent" examination; at lower doses there were differences in GPA ratings, demonstrating a less robust bowel cleansing. The results indicate that split doses more than 36 g/36 g result in significantly better colon cleansing than lower split doses, and especially lower single doses. Further, when one takes into account the more stringent criteria used in this study to assess the preparation results (i.e., GPA and RSS scales), the results obtained are even more dramatic.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for colonic cleansing comprising administering to a subject a first dose comprising from about 36 to about 72 g of L-glucose, and a second dose comprising from about 36 to about 72 g of L-glucose within a 24 hour period.

2. The method of claim 1, wherein the first dose is administered the night before the subject undergoes a colonoscopy, and the second dose is administered the morning of, but prior to, the colonoscopy.

3. The method of claim 1, wherein the L-glucose is L-glucose monohydrate.

4. The method of claim 3, wherein the first dose comprises about 52.8 g L-glucose monohydrate, and the second dose comprises about 52.8 g L-glucose monohydrate.

5. The method of claim 4, wherein the first dose is administered the night before the subject undergoes a colonoscopy, and the second dose is administered the morning of, but prior to, the colonoscopy.

6. The method of claim 4, wherein each dose of L-glucose monohydrate is dissolved in about 8 ounces of water.

7. The method of claim 1, wherein the first dose comprises from about 45 g to about 55 g of L-glucose, and the second dose comprises from about 45 g to about 55 g of L-glucose.

8. The method of claim 1, wherein the first dose comprises at least about 48 g of L-glucose, and the second dose comprises at least 48 g of L-glucose.

9. The method of claim 1, wherein the two doses are administered to the subject is prior to the subject undergoing a colonoscopy.

10. A method for colon cleansing in a subject comprising:
   (a) administering to the subject an aqueous solution containing from about 36 to about 72 g L-glucose (based on the weight of base L-glucose) at night, and
   (b) administering to the subject an aqueous solution containing from about 36 to about 72 g L-glucose the following morning.

11. The method of claim 10, wherein the subject is undergoing a colonoscopy, step (a) is performed the night before the colonoscopy, and step (b) is performed the morning of, but prior to, the colonoscopy.

12. The method of claim 10, wherein the L-glucose is L-glucose monohydrate.

13. The method of claim 12, wherein each aqueous solution is prepared by dissolving L-glucose monohydrate in water.

14. A method for colon cleansing in a subject undergoing a colonoscopy comprising:
   (a) administering to the subject an aqueous solution containing about 48 g L-glucose (based on the weight of base L-glucose) the night before the colonoscopy, and
   (b) administering to the subject an aqueous solution containing about 48 g L-glucose the morning of, but prior to, the colonoscopy.

15. The method of claim 14, wherein the L-glucose is L-glucose monohydrate.

16. The method of claim 15, wherein each aqueous solution is prepared by dissolving L-glucose monohydrate in water.

17. The method of claim 16, wherein each dose of L-glucose monohydrate is dissolved in about 8 ounces of water.

\* \* \* \* \*